United States Patent [19]

Ramachandran

[11] Patent Number: 4,552,964
[45] Date of Patent: Nov. 12, 1985

[54] 4-(1-CHLOROCYCLOHEX-3-ENYL)PYRIDINES AND PREPARATION OF 1-ALKYL-1,4-DIHYDRO-4-OXO-7-(4-PYRIDYL)-3-QUINOLINECARBOXYLIC ACID

[75] Inventor: Venkataraman Ramachandran, Baton Rouge, La.

[73] Assignee: Ethyl Corporation, Richmond, Va.

[21] Appl. No.: 532,703

[22] Filed: Sep. 16, 1983

[51] Int. Cl.[4] .................. C07D 215/16; C07D 211/72; C07D 211/70
[52] U.S. Cl. .................................... 546/156; 546/346; 546/329
[58] Field of Search ................ 546/345, 156, 346, 329

[56] References Cited
U.S. PATENT DOCUMENTS 3,753,993  8/1973  Lesher et al. ........................ 546/345
3,907,808  9/1975  Lesher et al. ........................ 546/345
4,118,557  10/1978 Lesher ................................. 546/345

OTHER PUBLICATIONS

Conrow et al., Deductive Organic Chemistry, Addison-Wesley Publishing Co., Inc., Reading, Mass., 1966, p. 171.
The Journal of General Chemistry of the U.S.S.R., vol. 26, No. 1, 1956.

Primary Examiner—Henry R. Jiles
Assistant Examiner—Robert C. Whittenbaugh
Attorney, Agent, or Firm—Donald L. Johnson; John F. Sieberth; Patricia J. Hogan

[57] ABSTRACT

A 4-(1-chlorovinyl)pyridine, preferably 4-(1-chlorovinyl)pyridine itself, is reacted with a butadiene, preferably chloroprene, to prepare a 4-(1-chlorocyclohex-3-enyl)pyridine. The preferred products are useful as intermediates in the preparation of antibacterial 1-alkyl-1,4-dihydro-4-oxo-7-pyridinyl-3-quinolinecarboxylic acids.

8 Claims, No Drawings

4-(1-CHLOROCYCLOHEX-3-ENYL)PYRIDINES AND PREPARATION OF 1-ALKYL-1,4-DIHYDRO-4-OXO-7-(4-PYRIDYL)-3-QUINOLINECARBOXYLIC ACID

FIELD OF INVENTION

This invention relates to 4-(1-chlorocyclohex-3-enyl)-pyridines, a process for preparing them, and processes for preparing derivatives thereof.

BACKGROUND

Petrov et al., *Journal of General Chemistry of the USSR* (English Translation), Vol. 26, No. 1, pp. 49–51 (January, 1956) teach the reaction between 4-vinylpyridine and a diene, such as butadiene or isoprene, to form a Diels-Alder product.

Copending applications Ser. No. 300,046, filed Sept. 8, 1981, in the name of Thomas J. Walter (Walter I), now U.S. Pat. No. 4,405,792 and Ser. No. 497,026, filed May 23, 1983, in the name of V. Ramachandran (Ramachandran I), disclose Diels-Alder reactions between haloprenes and 4-vinylpyridines, preferably in the presence of a boron trifluoride catalyst, to form 4-(halocyclohex-3-enyl)pyridines which are mixtures of 4-(4-halocyclohex-3-enyl)pyridine and 4-(3-halocyclohex-3-enyl)pyridine isomers in a mol ratio of about 65:35.

Since:

(1) an objective of Walter I and Ramachandran I is to form 4-(halocyclohex-3-enyl)pyridines useful in the synthesis of the antibacterial 1-alkyl-1,4-dihydro-4-oxo-7-pyridinyl-3-quinolinecarboxylic acids of Sterling Drug's U.S. Pat. Nos. 3,753,993 (Lesher et al.), 3,907,808 (Lesher and Carabateas), and 4,118,557 (Lesher), (2) 4-(4-halocyclohex-3-enyl)pyridines are the 4-(halocyclohex-3-enyl)pyridine isomers that are useful in this regard, and (3) the inherent formation of a substantial amount of the 4-(3-halocyclohex-3-enyl)pyridine isomers in their processes reduces the yield of 4-(4-halocyclohex-3-enyl)pyridine and derivatives that might otherwise be obtained in the practice of their inventions, it would be advantageous to modify their processes to provide a more favorable isomer distribution. It would be particularly advantageous to provid a Diels-Alder reaction that would not only lead to this more favorable isomer distribution in the preparation of 4-(halocyclohex-3-enyl)pyridines but also be useful in the preparation of other adducts.

SUMMARY OF INVENTION

An object of this invention is to provide novel 4-(1-chlorocyclohex-3-enyl)pyridines and derivatives thereof.

Another object is to provide novel Diels-Alder reactions for preparing the 4-(1-chlorocyclohex-3-enyl)pyridines.

A further object is to provide processes for preparing derivatives of the 4-(1-chlorocyclohex-3-enyl)pyridines.

These and other objects are attained by reacting a 4-(1-chlorovinyl)pyridine with a butadiene and, when appropriate, converting the resultant Diels-Alder adduct to a desired derivative thereof.

DETAILED DESCRIPTION 4-(1-Chlorovinyl)pyridines utilizable in the practice of the invention are 4-(1-chlorovinyl)pyridine and salts thereof with relatively strong acids, i.e., acids having dissociation constants of at least about $1.7 \times 10^{-5}$, preferably at least about $1.0 \times 10^{-1}$, at 25° C. (Acids having such dissociation constants include, e.g., inorganic acids, such as sulfuric, hydrochloric, hydrobromic, hydrofluoric, hydroborofluoric, etc., and organic acids, such as methanesulfonic, acetic, chloroacetic, dichloroacetic, etc.) These compounds may be prepared by any suitable technique but are preferably prepared by the process of copending application Ser. No. 532,700, filed Sept. 16, 1983, in the name of V. Ramachandran (Ramachandran II), the teachings of which are incorporated herein by reference. The preferred 4-(4-chlorovinyl)pyridine is 4-(4-chlorovinyl)pyridine itself.

The butadiene that is reacted with the 4-(4-chlorovinyl)pyridine is a substituted or unsubstituted conjugated diene having an aliphatic chain of four carbons, e.g., butadiene-1,3, isoprene, or a haloprene, i.e., a 2-halobutadiene wherein the halo substituent is chloro, bromo, iodo, or fluoro. In a preferred embodiment of the invention, the butadiene is a haloprene, most preferably chloroprene.

Except for the use of the aforementioned dienes and dienophiles, the process is conducted by known Diels-Alder techniques, such as the processes of Walter I and Ramachandran I, the teachings of which are incorporated herein by reference. Thus, it is preferred that the reactants be employed in substantially equimolar amounts, i.e., about 0.75–2, preferably about one, molar proportion of the butadiene per molar proportion of the 4-(1-chlorovinyl)pyridine, and that they be reacted together at a temperature of about 100°–150° C., preferably about 120°–130° C., under autogenous pressure in a suitable solvent. In the practice of the invention, it is generally preferred that the solvent be a halogenated hydrocarbon, such as methylene chloride, that is liquid under the reaction conditions. It is also generally preferred that the reaction be conducted in the presence of a boron trifluoride catalyst as in Ramachandran I.

The process results in the formation of 4-(1-chlorocyclohex-3-enyl)pyridines corresponding to the formula:

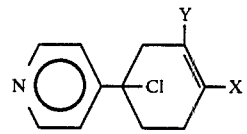

wherein one of X and Y is hydrogen and the other is hydrogen, halo (preferably chloro), or alkyl (preferably methyl). When the 4-(1-chlorocyclohex-3-enyl)pyridines are prepared from butadienes bearing substitutents to form compounds wherein X or Y is halo or alkyl, they are generally produced as isomeric mixtures; and it is an advantage of the invention that the isomeric mixtures produced from haloprenes, i.e., mixtures of 4-(1-chloro-4-halocyclohex-3-enyl)pyridine and 4-(1-chloro-3-halocyclohex-3-enyl)pyridine, contain these isomers in a ratio favorable toward the production of the aforementioned bactericides. It has been found that the reaction of a haloprene with a 4-(1-chlorovinyl)pyridine results in the formation of these isomers in a mol ratio of about 95:5, with the 4-halo compound predominating.

Once formed, the products of the invention may be subjected to conventional reactions to provide derivatives when desired—derivatives likely to be desired being the 4-(4-halophenyl)pyridines of Walter I and Ramachandran I. As in these references, isomeric mixtures may be separated before being subjected to further reactions; but they are generally kept in admixture when, e.g., the 4-(1-chloro-4-halocyclohex-3-enyl)pyridine is to be aromatized to the corresponding 4-(4-halophenyl)pyridine as in Walter I and Ramachandran I. Then, when other derivatives are desired, they may be subjected to the appropriate reactions, e.g., the reactions taught in copending application Ser. No. 511,887, filed July 8, 1983, in the name of Thomas J. Walter (Walter II), the teachings of which are incorporated herein by reference.

In general, when one or more of the processes of Walter II are to be employed, the 4-(4-halophenyl)pyridine—alone or in admixture with a 4-(3-halophenyl)pyridine—is nitrated to a 4-(4-halo-3-nitrophenyl)pyridine, preferably 4-(4-chloro-3-nitrophenyl)pyridine, which may then be reduced to a 4-(3-aminophenyl)pyridine, such as 4-(3-aminophenyl)pyridine itself. Then, when antibacterial agents, such as the 1-alkyl-1,4-dihydro-4-oxo-7-pyridinyl-3-quinolinecarboxylic acids of Lesher, Lesher et al., and Lesher and Carabateas, are desired, they—or their intermediates—may be prepared by subjecting the 4-(3-aminophenyl)pyridines to suitable reactions which may be conducted by known techniques. For example:

(1) the 4-(3-aminophenyl)pyridine may be reacted with a dialkyl ethoxymethylenemalonate to form a dialkyl 3-(4-pyridyl)anilinomethylenemalonate, which may be cyclized to an alkyl 1,4-dihydro-4-oxo-7-(4-pyridyl)-3-quinolinecarboxylate, which in turn may be N-alkylated to an alkyl 1-alkyl-1,4-dihydro-4-oxo-7-(4-pyridyl)-3-quinolinecarboxylate, which may then be hydrolyzed to a 1-alkyl-1,4-dihydro-4-oxo-7-(4-pyridyl)-3-quinolinecarboxylic acid, as in Lesher et al. and Lesher and Carabateas, (2) the 4-(3-aminophenyl)pyridine may be reductively alkylated, or it may be acylated and then reduced, as in Lesher, to form a 4-(3-alkylaminophenyl)pyridine, otherwise designated as a 3-(4-pyridyl)-N-alkylaniline, which may then be (a) subjected to the reaction steps of Lesher et al. and Lesher and Carabateas without the need for their N-alkylation step or (b) subjected to reaction with a cyclic alkylidenyl alkoxymethylenemalonate, etc., as in Lesher, to form the antibacterial agent, or (3) either of the above procedures may be terminated at the end of any step to recover a desired product for use in any other desired process, etc.

As in Walter II, when an acylated 4-(3-aminophenyl)pyridine is desired, it is sometimes convenient to combine the reduction and acylation steps, e.g., by reducing the 4-(4-halo-3-nitrophenyl)pyridine with hydrogen in the presence of sodium acetate, a palladium-on-carbon catalyst, and glacial acetic acid—a process which leads to a high yield of 4-(3-aminophenyl)pyridine at 60°–70° C. but which produces substantial yields of 4-(3-acetamidophenyl)pyridine when conducted for a sufficient time at temperatures near 80° C. Alternatively and more efficiently, 4-(3-acetamidophenyl)pyridine can be produced by including acetic anhydride in the reduction recipe.

The following examples are given to illustrate the invention and are not intended as a limitation thereof.

EXAMPLE

Part A

A reaction mixture containing 1.4 g of 4-(1-chlorovinyl)pyridine, 20 ml of methylene chloride, 1.32 g of chloroprene, and 1.4 g of boron trifluoride was heated at 120°–130° C. for 10 hours. The product was leached with 100 ml of 1N HCl until completely dissolved, then extracted twice with 50 ml aliquots of ether, neutralized to a pH of 8 with 50% sodium hydroxide, and extracted with three 100 ml portions of methylene chloride. The combined methylene chloride layer was dried, filtered, and evaporated to leave behind an oil comprising a crude mixture of 4-(1,4-dichlorocyclohex-3-enyl)pyridine and 4-(1,3-dichlorocyclohex-3-enyl)pyridine.

Part B

The crude reaction product of Part A was treated with about 50 mg of palladium-on-carbon in about 20 ml of nitrobenzene and slowly heated to about 190° C. in about four hours. The reaction mixture was taken up in about 50 ml of methanol and filtered. The excess methanol from the filtrate was evaporated, leaving a dark solution which was taken up in 100 ml of ether and extracted with 100 ml of 1N HCl. The aqueous layer was washed with two 50 ml aliquots of ether, neutralized with 50% sodium hydroxide to a pH of about 8–9, and extracted with three 100 ml portions of methylene chloride. The combined methylene chloride layer was dried, filtered, and evaporated to give an oil which analysis showed to contain 4-(4-chlorophenyl)pyridine and 4-(3-chlorophenyl)pyridine in a mol ratio of 93:7.

It is obvious that many variations may be made in the products and processes set forth above without departing from the spirit and scope of this invention.

I claim:

1. A 4-(1-chlorocyclohex-3-enyl)pyridine corresponding to the formula:

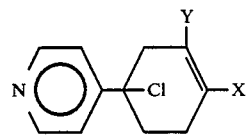

wherein one of X and Y is hydrogen and the other is hydrogen, halo or an alkyl of 1–6 carbons.

2. The 4-(1-chlorocyclohex-3-enyl)pyridine of claim 1 wherein X or Y is chloro.

3. The 4-(1-chlorocyclohex-3-enyl)pyridine of claim 2 wherein X is chloro.

4. The 4-(1-chlorocyclohex-3-enyl)pyridine of claim 1 wherein X or Y is an alkyl group of 1–6 carbons.

5. The 4-(1-chlorocyclohex-3-enyl)pyridine of claim 4 wherein the alkyl group is methyl.

6. The 4-(1-chlorocyclohex-3-enyl)pyridine of claim 5 wherein X is methyl.

7. In a process for preparing a 1-alkyl-1,4-dihydro-4-oxo-7-(4-pyridyl)-3-quinolinecarboxylic acid by:

(a) aromatizing a 4-(4-halocyclohex-3-enyl)pyridine to a 4-(4-halophenyl)pyridine, (b) nitrating the 4-(4-halophenyl)pyridine to a 4-(4-halo-3-nitrophenyl)pyridine, (c) reducing the 4-(4-halo-3-nitrophenyl)pyridine to a 4-(3-aminophenyl)pyridine, (d) reacting the 4-(3-aminophenyl)pyridine with a dialkyl ethoxymethylenemalonate to form a dialkyl 3-(4-pyridyl)anilinomethylenemalonate, (e) cyclizing the dialkyl 3-(4-pyridyl)anilinomethylenemalonate to an alkyl 1,4-dihydro-4-oxo-7-(4-pyridyl)-3-quinolinecarboxylate, (f) N-alkylating the alkyl 1,4-dihydro-4-oxo-7-(4-pyridyl)-3-quinolinecarboxylate to an alkyl 1-alkyl-1,4-dihydro-4-oxo-7-(4-pyridyl)-3-quinolinecarboxylate, and (g) hydrolyzing the alkyl 1-alkyl-1,4-dihydro-4-oxo-7-(4-pyridyl)-3-quinolinecarboxylate, the improvement which comprises using as the 4-(4-halocyclohex-3-enyl)pyridine a 4-(1-chloro-4-halocyclohex-3-enyl)pyridine prepared by reacting a haloprene with a 4-(1-chlorovinyl)pyridine in the presence of a boron trifluoride catalyst.

8. In a process for preparing a 1-alkyl-1,4-dihydro-4-oxo-7-(4-pyridyl)-3-quinolinecarboxylic acid by (a) aromatizing a 4-(4-halocyclohex-3-enyl)pyridine to a 4-(4-halophenyl)pyridine, (b) nitrating the 4-(4-halophenyl)pyridine to a 4-(4-halo-3-nitrophenyl)pyridine, (c) reducing the 4-(4-halo-3-nitrophenyl)pyridine to a 4-(3-aminophenyl)pyridine, (d) converting the 4-(3-aminophenyl)pyridine to a 3-(4-pyridyl)-N-alkylaniline, (e) reacting the 3-(4-pyridyl)-N-alkylaniline with a dialkyl ethoxymethylenemalonate to form a dialkyl 3-(4-pyridyl)-N-alkylanilinomethylenemalonate, (f) cyclizing the dialkyl 3-(4-pyridyl)-N-alkylanilinomethylenemalonate to an alkyl 1-alkyl-1,4-dihydro-4-oxo-7-(4-pyridyl)-3-quinolinecarboxylate, and (g) hydrolyzing the alkyl 1-alkyl-1,4-dihydro-4-oxo-7-(4-pyridyl)-3-quinolinecarboxylate, the improvement which comprises using as the 4-(4-halocyclohex-3-enyl)pyridine a 4-(1-chloro-4-halocyclohex-3-enyl)pyridine prepared by reacting a haloprene with a 4-(1-chlorovinyl)pyridine in the presence of a boron trifluoride catalyst.

* * * * *